US00PP16079P3

(12) United States Plant Patent
Lintott

(10) Patent No.: US PP16,079 P3
(45) Date of Patent: Nov. 1, 2005

(54) *CHRYSANTHEMUM* PLANT NAMED 'NIGHTHAWK YELLOW'

(50) Latin Name: *Chrysanthemum morifolium*
Varietal Denomination: Nighthawk Yellow

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 17 days.

(21) Appl. No.: 10/693,364

(22) Filed: Oct. 24, 2003

(65) Prior Publication Data

US 2004/0083513 P1 Apr. 29, 2004

Related U.S. Application Data

(60) Provisional application No. 60/421,384, filed on Oct. 25, 2002.

(51) Int. Cl.[7] ..... A01H 5/00

(52) U.S. Cl. ..... Plt./289

(58) Field of Search ..... Plt./289, 287

(56) References Cited

U.S. PATENT DOCUMENTS

PP11,606 P 10/2000 Boeder ..... Plt./289

OTHER PUBLICATIONS

Royal Van Zanten Garden Mum Catalog 2002, listing *Chrysanthemum* variety 'Nighthawk lemon' and Nighthawk at pp. 6 (color pictures), 9 and 14.

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Nighthawk Yellow', having a domed, round habit and yellow decorative flowers. The new variety has good foliage presentation and weather resistance.

1 Drawing Sheet

Latin name of the genus and species: Botanical classification: *Chrysanthemum morifolium.*

Variety denomination: The new *Chrysanthemum* variety denomination is 'Nighthawk Yellow. '

BACKGROUND OF THE INVENTION

The present invention comprises a new and distinct cultivar of *Chrysanthemum* botanically known as *Chrysanthemum morifolium,* and referred to by the cultivar name 'Nighthawk Yellow. '

'Nighthawk Yellow' identified as 30219-1, originated from a naturally occurring whole plant mutation in a controlled planting of the unpatented variety 'Nighthawk' in Chichester, West Sussex, United Kingdom. The new variety 'Nighthawk Yellow' has been asexually reproduced by vegetative cuttings in Chichester, West Sussex, United Kingdom and the distinguishing characteristics are retained through successive generations of asexual reproduction.

BRIEF SUMMARY OF THE INVENTION

'Nighthawk Yellow' is a garden type of *Chrysanthemum* plant variety having a domed, round habit and yellow decorative flowers.

Comparison with Parent

Plants of the new *Chrysanthemum* variety 'Nighthawk Yellow' are similar to the parent variety 'Nighthawk' in plant habit and growth rate. In side-by-side comparisons in Chichester, West Sussex, United Kingdom, under commercial practice, plants of the new *Chrysanthemum* variety 'Nighthawk Yellow' differ from plants of the parent 'Nighthawk' in the following characteristic.

1. The new variety 'Nighthawk Yellow' produces yellow flowers whereas the parent 'Nighthawk' produces pink flowers.

Comparison with Other Varieties

Plants of the new *Chrysanthemum* variety 'Nighthawk Yellow' are similar to the patented variety 'Gold Crest' (U.S. Plant Pat. No. 11,606) in plant habit and growth rate. However, in side-by-side comparisons in Chichester, West Sussex, United Kingdom, under commercial practice, plants of the new *Chrysanthemum* variety 'Nighthawk Yellow' differed from plants of 'Gold Crest' in the following characteristics.

1. The new variety 'Nighthawk Yellow' produces clear yellow decorative flowers whereas 'Gold Crest' produces yellow/bronze flowers.
2. The new variety 'Nighthawk Yellow' produces smaller flowers than 'Gold Crest'.

BRIEF DESCRIPTION OF ILLUSTRATION

Typical specimens of the plant and flowers for the new *Chrysanthemum* variety 'Nighthawk Yellow' are shown in the accompanying digital photograph. The colors shown are as true as possible within the usual limits of this kind of illustration.

FIG. 1 is a whole plant view of the new variety 'Nighthawk Yellow' grown in a pot.

The plant shown in the illustration is 70 days from commencement of planting outdoors in mid-June.

DETAILED BOTANICAL DESCRIPTION

The following description of the new *Chrysanthemum* variety 'Nighthawk Yellow' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 65° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liter (8"). It has been observed that the shelf life of the new variety is about 26 days with a response time of about 10 weeks natural season. The new variety is suitable for growth in a temperature range of 50° F. to 75° F. The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed, Round, Spreading.
Height: 48–53 cm.
Width: 45–48 cm.
Branching characteristics: Free Branching, Spreading.
Length of lateral branches: 11–15 cm.
Number of breaks from pinch: 7–9.
Stem color: Near 137A.
Response time: 70 days.
Vigor: Medium/Tall.
Shelf life: 26 days.
Disease (susceptibility/resistance observed): None observed to date.
Pest (susceptibility/resistance observed): None observed to date.
Growth retardant type and treatment: No treatment necessary.
The plants were grown for 10 weeks in natural season conditions.
Propagation:
*Type.*—Vegetative Propagation via Stem Cuttings.
*Time to rooting.*—12 days with soil temperatures of 70° F.
*Rooting habit.*—Fine and Fibrous.

Foliage

Number of leaves per ateral branch: 7–11.
Compound or single: Single.
Arrangement of leaves: Alternate.
*Shape of leaf.*—Typically 5 lobed ovate.
*Size of leaf.*—Width (cm): 1.5–3.5 Length (cm): 3–5.
*Leaf apex.*—Acute.
*Base.*—Truncate.
*Attachment.*—Petioled.
*Aspect.*—Slightly Undulating.
*Margin.*—Palmately Lobed.
*Surface characteristics.*—Top: Slightly Pubescent. Bottom: Slightly Pubescent.
Petiole:
*Color.*—138B.
*Length.*—0.7–1 cm.
*Diameter.*—0.3–0.5 cm.
Venation: Net prominent mid vein at underside.
*Color.*—Upper side: near 138B. Under side: near 138C.
Color:
*Mature leaf, upper side.*—Near 137A; under side: near 137B.
*Young leaf, upper side.*—Near 137B; under side: near 137B.

Flower

Flower appearance: Matte.
Flower type: Decorative.
Flower form: Domed.
Flower shape: Round.
Flowering habit: Cyme.
Number of blossoms per branch: 7–11.
Inflorescence form: Corymibiform in form, in that the outer stalks are longer than the inner stalks, but flowering habit is cyme from the terminal flower first.
Depth of fully expanded blossoms: 2–3.5 cm.
Diameter of fully expanded blossoms: 2.5–4.5 cm.
Phyllaries:
*Number.*—28–30.
*Color.*—Near 136C.
*Length.*—6–8 mm.
*Width.*—1–2 mm.
*Texture/appearance.*—Pubescent.
Pedicel:
*Length.*—Terminal: 8 cm; lateral: 11 cm.
*Diameter.*—0.4–0.5 cm.
*Color.*—Near 136B.
*Surface.*—Pubescent.
*Habit.*—Straight.
*Strength.*—Medium.
Ray florets:
*Form/shape.*—Straight with oblong shape.
*Texture/appearance.*—Matte.
*Number per flower.*—190–220.
*Length.*—1.5–2.5 cm; Width: 3–6 mm.
*Apex.*—Rounded, Slightly Dentate.
*Base.*—Tubular.
*Margin.*—Entire.
Disc florets:
*Form/shape.*—Cylindrical.
*Texture/appearance.*—Shiny.
*Number per flower.*—2–3.
*Length.*—5–6 mm; Width: 1 mm.
*Diameter of disc.*—1–2 mm.
Fragrance: None.
Flower bud (at onset of color):
*Length.*—5–7 mm.
*Diameter.*—6–8 mm.
*Form/shape.*—Globular.
General flower color:
1. *Ray florets, upper side.*—Immature: near 9A. Mature: near 10A. Older/Fading: near 10C.
2. *Ray florets, under side.*—Immature: near 9A. Mature: near 10A. Older/Fading: near 10C.
3. *Disc florets.*—Immature: near 15A. Mature: near 15B. Older/Fading: near 15D.
4. *Bud.*—Near 145B.

Flower progression with age: Flowers fade uniformly with age and some florets become reflexing.
Lastingness of blooms: About 26 days.

Reproductive Organs

Gynoecium present on Ray and Disc florets.
Ray florets per individual flower:
*Pistil number.*—60–80 observed.
*Stigma color.*—Near 144D.
*Stigma shape.*—Forked.
*Style color.*—Near 144D.
*Style length.*—3 mm.

Disc florets per individual flower:
*Pistil number.*—2–3.
*Stigma color.*—144C.
*Stigma shape.*—Forked.
*Style color.*—Near 144D.
*Style length.*—3 mm.
Androecium: Not observed.
Fruit and seeds: None observed.

What is claimed is:

1. A new and distinct variety of *Chrysanthemum* plant, substantially as described and illustrated herein.

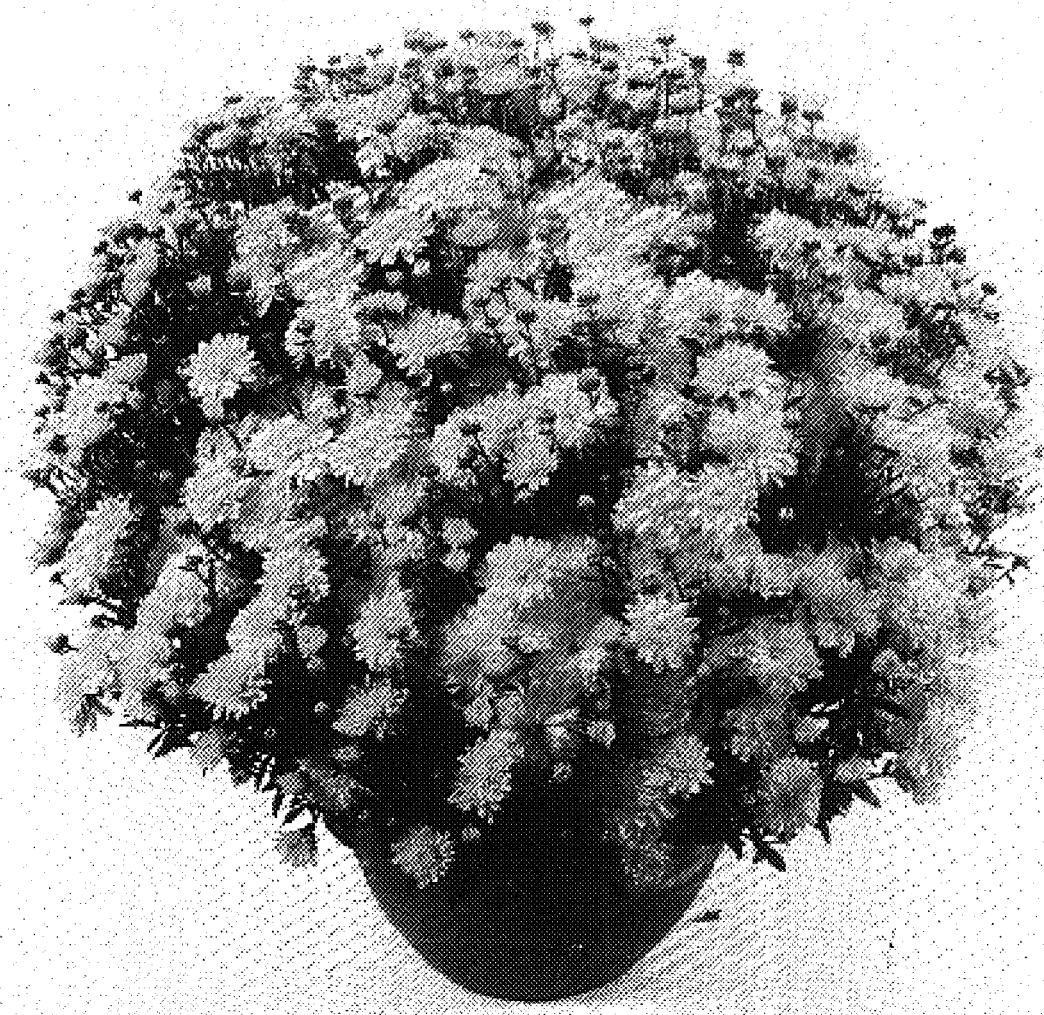

* * * * *